United States Patent [19]
Ramp et al.

[11] Patent Number: 5,968,999
[45] Date of Patent: Oct. 19, 1999

[54] BONE CEMENT COMPOSITIONS

[75] Inventors: Warren Kibby Ramp, Charlotte; Richard Dennis Peindl, Huntersville, both of N.C.

[73] Assignee: Charlotte-Mecklenburg Hospital Authority, Charlotte, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/959,498

[22] Filed: Oct. 28, 1997

[51] Int. Cl.$^6$ ...................................................... A61K 6/08
[52] U.S. Cl. ............................ 523/116; 523/114; 523/115
[58] Field of Search ..................................... 523/114, 115, 523/116

[56] References Cited

U.S. PATENT DOCUMENTS

| | | | |
|---|---|---|---|
| 3,789,051 | 1/1974 | Rees | 524/432 |
| 4,131,597 | 12/1978 | Blüethgen et al. | . |
| 4,197,215 | 4/1980 | Dudinyak | 526/216 |
| 4,211,742 | 7/1980 | Kato | 526/230.5 |
| 4,239,113 | 12/1980 | Gross et al. | . |
| 4,546,145 | 10/1985 | Kishida | 524/780 |
| 4,728,570 | 3/1988 | Ashman et al. | . |
| 4,789,709 | 12/1988 | Kato | 525/366 |
| 4,851,046 | 7/1989 | Low et al. | . |
| 5,037,445 | 8/1991 | Sander | 623/66 |
| 5,514,137 | 5/1996 | Coutts | 606/62 |

FOREIGN PATENT DOCUMENTS

| | | |
|---|---|---|
| 1431211 | 4/1976 | European Pat. Off. . |
| WO 94/17838 | 8/1994 | WIPO . |

OTHER PUBLICATIONS

Medium pH Modulates Matrix, Mineral, and Energy Metabolism in Cultured Chick Bones and Osteoblast–Like Cells, W. Ramp et al., Bone Miner. 24 (1994) pp. 59–73.

A Serum Substitute Promotes Osteoblast–Like Phenotypic Expression in Cultured Cells From Chick Calvariae, W. Ramp et al.; Bone and Mineral, 15 (1991) pp. 1–17.

Continuously Infused Calcium Hydroxide: Its Influence on Hard Tissue Repair, K. Freeman et al., Journal of Endodontics, vol. 20, No. 6, Jun. 1994, pp. 272–275.

The Effects of Calcium Hyudroxide on Bovine Pulp Tissue: Variations in pH and Calcium Concentration; T. Gordon et al., Journal of Endodontics, vol. 11, No. 4, Apr. 1985, pp. 156–160.

Oral Administration of Calcium Hydroxide Stimulates Bone Metabolism in the Femoral Diaphysis of Rats with Skeletal Unloading, M. Yamaguchi et al., Chem. Pharm. Bull. 39 (12). 1991, pp. 3365–3367.

Comparative Effect of Calcium Hydroxide and Hydroxyapatite on the Cellular Activity of Human Pulp Fibroblasts In Vitro, B. Alliot–Licht et al., Archs Oral Biol. vol. 39, No. 6, 1994, pp. 481–489.

Antibiotic–Impregnated Cement Use in U.S. Hospitals, D. Fish et al., Am. J. Hosp. Pharm. vol. 49 Oct. 1992, pp. 2469–2474.

Interaction of Tobramycin and pH in Cultured Chick Tibiae, T. Murakami et al., Trans. Orthop. Res. Soc., 20:261, 1995, pp. 261–43.

Calcium Hydroxide Amellorates Tobramycin Toxicity in Cultured Chick Tibiae, T. Murakami et al., Trans. Orthop. Res. Soc. 21:293, 1996, p. 293.

*Primary Examiner*—Paul R. Michl
*Attorney, Agent, or Firm*—Alston & Bird LLP

[57] ABSTRACT

There is provided a polymethylmethacrylate (PMMA) bone cement composition that includes the addition of from about 10% by weight to about 30% by weight of calcium hydroxide. The bone cement is used for orthopaedic procedures, injuries, or disease states that have compromised the metabolism of local hard and soft tissues, largely due to an acidic environment. In an aqueous environment, the calcium hydroxide is slowly released from pores in the polymer matrix as calcium and hydroxyl ions to provide a method for stimulating healing by maintaining or elevating local pH in the tissues adjacent to bone cement. It has also been found that the calcium hydroxide ameliorates the toxic effects of antibiotics which are often included in the bone cement.

23 Claims, 4 Drawing Sheets

BONE CEMENT COMPOSITIONS

BACKGROUND OF THE INVENTION

The present invention relates to a composition for preparing bone cement. More specifically, the present invention relates to bone cement compositions containing calcium hydroxide, a sparingly soluble strong base in an aqueous environment.

There are a number of conditions in which hard and soft tissues may be compromised due to decreased local environmental pH such as open and closed fractures, infections, decreased tissue perfusion, and disease states. Regarding these conditions, bone cement has been commonly used as a structural component, an adjuvant therapeutic agent, and a drug delivery system.

One type of bone cement is made by blending polymerizable materials such as homopolymers or copolymers of methylmethacrylate together with suitable liquid monomers, primarily methylmethacrylate, and a catalyst to form a plastic paste which is inserted into the body and cured. An example of such a bone cement is shown in British Patent No. 1,431,211, which discloses a bone cement composition having a liquid component comprising (a) at least 50% of monomeric methacrylate, up to 5% of a tertiary amine and between 10% and 45% of at least one $C_2$–$C_6$ alkyl methacrylate, (b) a powder component including polymethylmethacrylate, and (c) a catalytic system such as one including dimethyl-p-toluidine. The British patent warns of the problems that can occur to the bone tissue if the temperature of the exothermic reaction of the polymer during curing rises above a critical temperature.

As a result of trauma and during the rehabilitation of bones after surgery, infection often occurs. To combat the infection, bone cements may also include antibiotics. However, because of the high temperatures caused by the polymer mixture during curing (i.e., during polymerization of polymethylmethacrylate during arthroplasty), the cytotoxicity of liquid methylmethacrylate monomer used for the polymerization, and the high toxic doses of antibiotics needed to treat bone infections, use of polymethylmethacrylate bone cement can lead to locally compromised or necrotic bone.

It is therefore an object of the present invention to provide a method for stimulating bone cell metabolism by maintaining or elevating local pH in the bone adjacent to bone cement.

Another object of the present invention is to provide a bone cement composition that ameliorates the toxic effect of an antibiotic as it is released from the bone cement composition.

SUMMARY OF THE INVENTION

It has been found that when polymethylmethacrylate (PMMA) bone cement composition utilized for orthopaedic procedures contains from about 10% by weight to about 30% by weight of calcium hydroxide, the calcium hydroxide dissolves and calcium and hydroxyl ions are slowly released from the porous cement matrix. This release has been shown to elevate the metabolism of the bone-forming cells (osteoblasts) resulting in augmented new bone formation. It has also been found that the calcium hydroxide ameliorates the toxic effects of antibiotics which are often included in the bone cement.

In one embodiment of the invention there is provided a polymethylmethacrylate (PMMA) bone cement composition containing a mixture of copolymers of methylmethacrylate and methacrylate in an amount of from about 70% to about 90% of the weight of the composition, and a catalyst to speed polymerization, and from about 10% to about 30% by weight of calcium hydroxide. The calcium hydroxide particles should be of a size such that they fit into the pores normally produced in the PMMA matrix. The bone cement may also contain additives for radiopacity such as up to about 20% by weight barium sulfate.

In another embodiment of this invention the above described polymethylmethacrylate (PMMA) bone cement composition containing calcium hydroxide may also contain an antibiotic.

Examples of such applications include implant seating for arthroplasty, filling of bony defects resulting from trauma or tumor resection, and antibiotic delivery systems for treating osteomyelitis.

BRIEF DESCRIPTION OF THE DRAWINGS

Other objects, features, and advantages of the present invention will become apparent from the following detailed description of the invention taken in conjunction with the accompanying drawings, in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

It has been found that the rate of metabolism of osteoblasts, the bone-forming cells, is directly related to the pH of their microenvironment. Thus, bone formation is stimulated if acid conditions are not allowed to prevail or if the local pH is slightly elevated.

A slow-release calcium hydroxide delivery system for stimulating bone growth, healing, and metabolism is prepared by forming a mixture of copolymers of methylmethacrylate and methacrylate and up to 30% about by weight of the total composition of calcium hydroxide. Preferably, the amount of calcium hydroxide is from about 12% by weight to about 17% by weight, with 15% by weight calcium hydroxide being most preferred. It was found that release of calcium hydroxide releases from polymethylmethacrylate bone cement over an extended period of time and markedly stimulates bone metabolism.

The polymethylmethacrylate bone cement composition is made by reacting a powder component such as polymethylmethacrylate with a liquid monomer component and a catalyst. An admixture of commercially-available polymethylmethacrylate bone cement may be used. One such example may be obtained from Zimmer Corp., Warsaw, Ind. The preferred liquid polymerizable monomers are methacrylic acid compounds such as its esters, preferably methylmethacrylate, ethylmethacrylate, butyl methacrylate, isobutyl methacrylate, 2-hydroxy ethyl methacrylate and the amides of methacrylic acid. Copolymers of methacrylic acid compounds with other polymerizable monomers may also be used. The liquid component generally comprises at least 50% of monomeric methacrylate, up to 5% of a tertiary amine and between 10% and 45% of at least one $C_2$–$C_6$ alkyl methacrylate. The monomeric component usually contains small amounts of hydroquinone in amounts up to about 150 ppm, preferably 25 to 100 ppm as a stabilizer.

The polymer should also contain a catalytic system to accelerate hardening of the polymer within a suitable time such as 15 minutes or less. Any suitable hardening system may be used. Such catalyst systems may include an inorganic peroxy compound, such as benzoylperoxide or dibenzoylperoxide as a catalyst, with a reducing agent, e.g., dimethyl-p-toluidine. Other curing catalyst include for example azobisisobutyronitrile, ammonium and other peroxysulfates, substituted benzoylperoxides, for instance 2-clorobenzoylperoxide. Curing or hardening may also be obtained by irradiation.

The polymethylmethacrylate bone cement composition may also include radiopacity additives which when the bone cement is cured provide contrast when the portion of the body including the bone cement is x-rayed, e.g., barium sulfate or zirconium dioxide. The amount of barium sulfate added may be from about 1.0% to about 20.0% by weight, preferably about 10.0% by weight.

Calcium hydroxide released from PMMA bone cement stimulates bone glucose metabolism and collagen synthesis in culture. It has also been found that calcium hydroxide co-released with tobramycin from PMMA bone cement completely ameliorates the toxic effects of the antibiotic.

Many antibiotics are suitable and the following are noted by way of illustration. Aminoglycoside-antibiotics such as Amikacin, Butirosine, Gentamycin, Neomycin and Tobramycin; Erythromycine; lactone-antibiotics, such as Novobiocin; leucomycines, such as Josamycin, Spiramycin; lincomycines, such as Clindamycin; penicilins such as Amoxicillin, Ampicillin, Furoxacillin; peptid-antibiotics such as Bacitracin; Streptomycine; Tetracycline; cephalosporine, such as Cefalotin. The aminoglycosid-antibiotics, particularly Tobramycin and its salts, are especially suitable due to their broad spectrum antibacterial action and their temperature stability.

Before adding the monomer solution to initiate polymerization, the powder component is mixed to contain $Ca(OH)^2$ at 10–30% (w/w). The size of the calcium hydroxide particles should be such as to fit within the normal porous cavities produced in prepared and cured polymethylmethacrylate (approximately 1/25th the diameter of the powdered polymethylmethacrylate (PMMA) particles).

Figure 2:
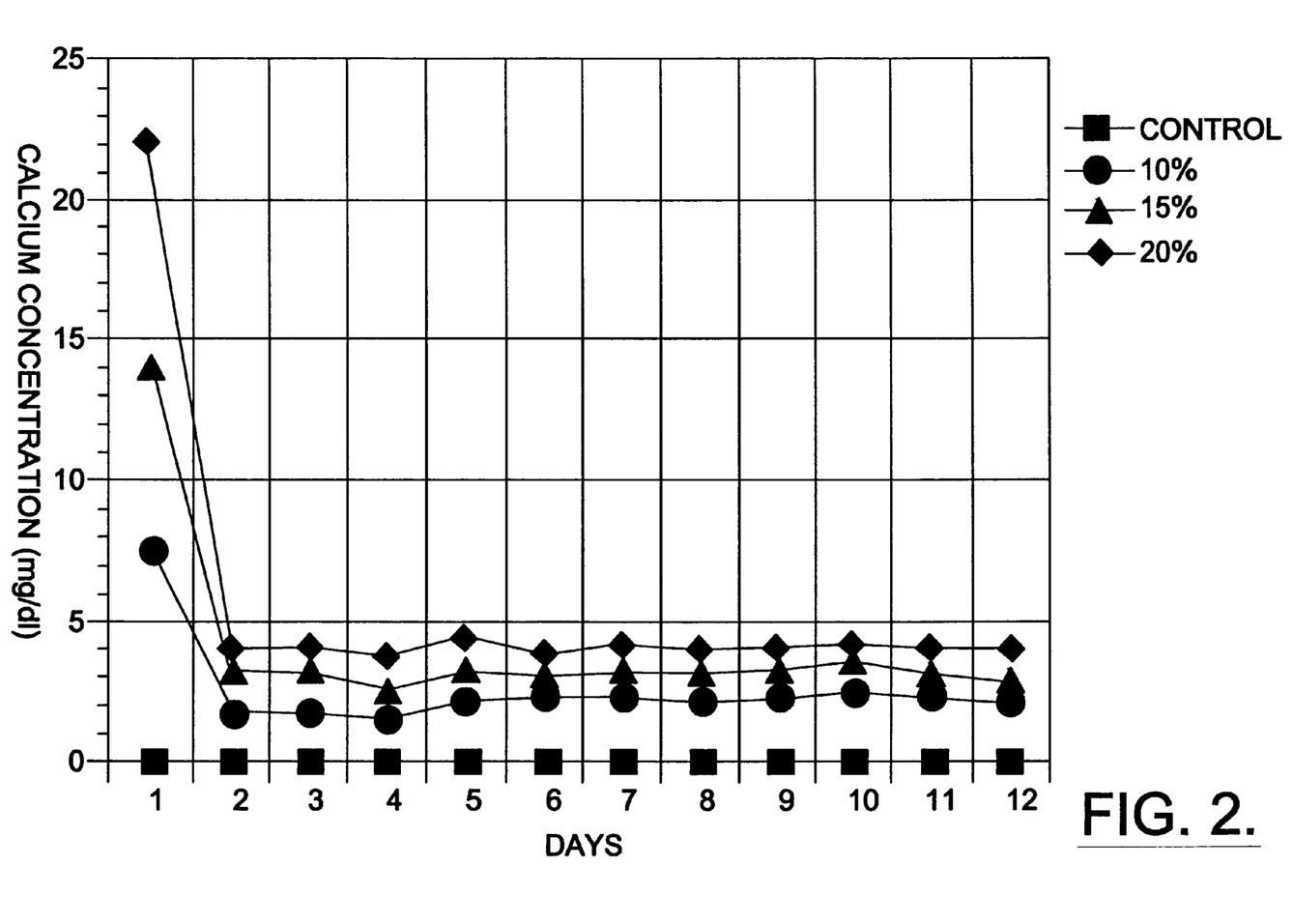
FIG. 2 illustrates the calcium hydroxide concentration (mg/dl) released each day from polymethylmethacrylate bone cement composition containing various levels of calcium hydroxide (wherein each specimen was immersed in 15 ml. of NaCl and incubated at 37° C. on a rocker platform)

Sterile polymethylmethacrylate (PMMA) powdered mixture containing calcium hydroxide is used in like fashion to PMMA without calcium hydroxide. It is polymerized in molds or in vivo for the applications described above. As shown in FIG. 2, in vitro the calcium hydroxide gradually dissolves and leaches into the surrounding medium leaving behind porous cavities in the PMMA polymer which are normally produced as part of the curing process.

EXAMPLE

This example describes a bone cement composition of the present invention.

A bone cement was prepared consisting of 80 gram packages of a sterile, powdered mixture of polymethylmethacrylate (89.25%, w/w), barium sulfate (10.00%), and benzoyl peroxide (0.75%) plus a 40 ml. ampule of sterile solution containing methylmethacrylate monomer (97.25%), v/v), N,N-dimethyl-p-toluidine (2.75%), and hydroquinone (75 ppm). Before adding the monomer solution to initiate polymerization, the polymethylmethacrylate powder was manually mixed to contain tobramycin sulfate (Nebcin, Eli Lily, Indianapolis, Ind.) at 5% (w/w) and $Ca(OH)_2$ (ACS reagent, sigma Co., St. Louis, Mo.). Beads containing different amounts of $Ca(OH)_2$ were made at 10.0%, 15%, and 20.0% (w/w). The complete mixtures were injected into bead or disk molds and allowed to polymerize. The beads were 6 mm in diameter and each contained 18 mg of tobramycin sulfate.

The mixture was pliable and formable after one minute and then was compacted into a mold to form non-porous pieces. The polymerization was completed in about 10 minutes.

Figure 1A:
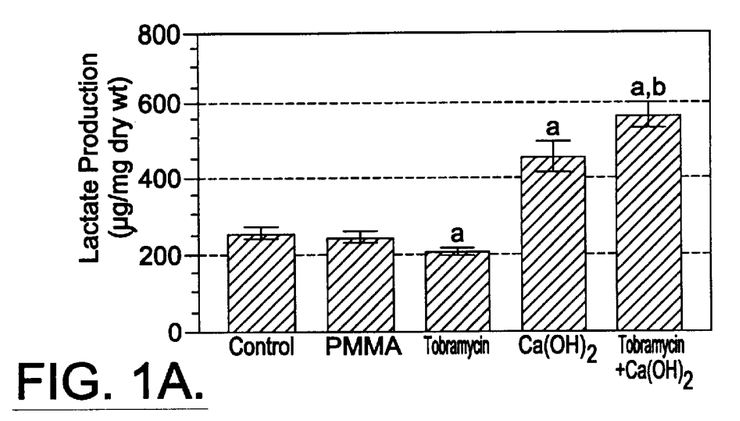
FIG. 1 illustrates the effects of calcium hydroxide-and/or antibiotic-impregnated polymethylmethacrylate beads on the metabolism of cultured bones. (A) energy metabolism via glycolysis, (B) total protein synthesis, (C) collagen synthesis, (D) medium pH, (F) medium calcium concentration.
Figure 1B:
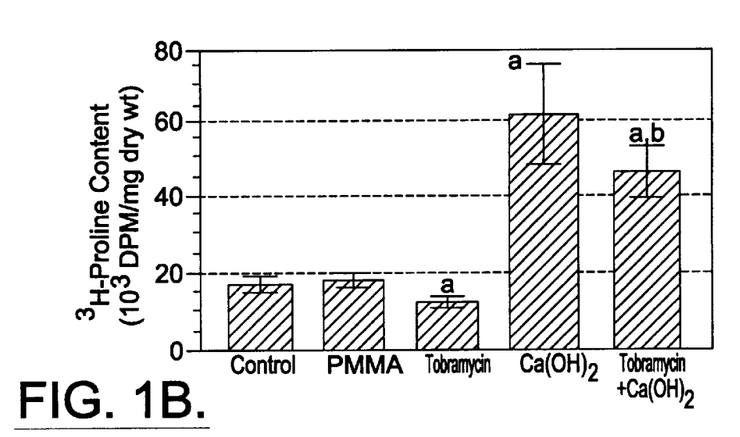
Figure 1C:
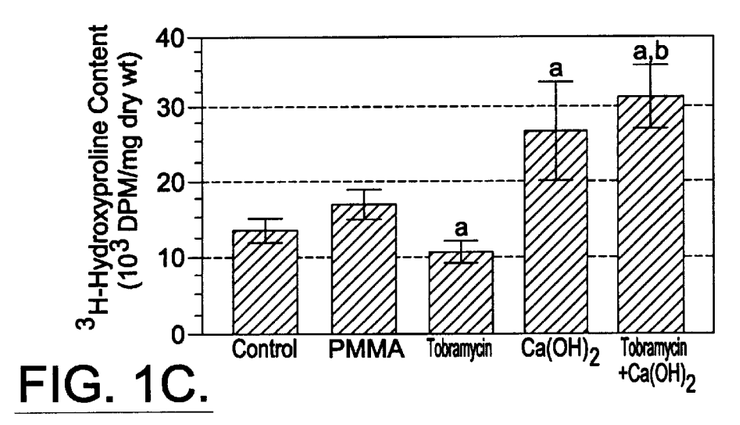

FIGS. 1A–C demonstrate bone metabolism (glycolysis, total protein synthesis, and collagen synthesis) at day 3 when bones were co-incubated without (control) or with non-impregnated, tobramycin-impregnated, $Ca(OH)_2$-impregnated, or tobramycin plus $Ca(OH)_2$-impregnated PMMA beads. In this experiment, the medium was not changed for 3 days to more closely mimic the conditions of an infected area in vivo, e.g., accumulation of metabolic waste products and acids due to hypoxic conditions from poor tissue perfusion and from bacterial activity. For all three variables, tobramycin-impregnated beads depressed bone metabolism compared to control tibiae (lactate production, 18%, FIG. 2A; $^3$H-proline content, 28%, FIG. 2B; and $^3$H-hydroxyproline content, 23%, FIG. 2C, p<0.05). In contrast, $Ca(OH)_2$ or tobramycin plus $Ca(OH)_2$ beads produced highly stimulated bone metabolism compared to control, even when tobramycin was present in the combination beads (lactate production, 80 or 121%; $^3$H-proline content, 267 or 185%; and $^3$H-hydroxyproline content, 100 or 135%, respectively, p<0.05). Bone metabolism was not affected by PMMA without additives (p$\geq$0.05).

Figure 1D:
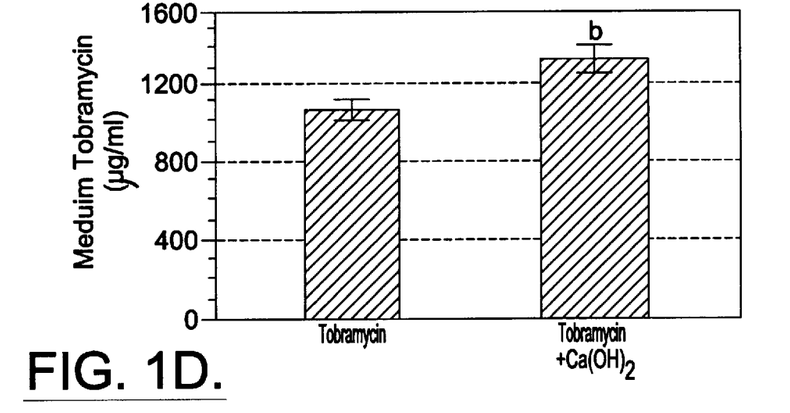
Figure 1E:
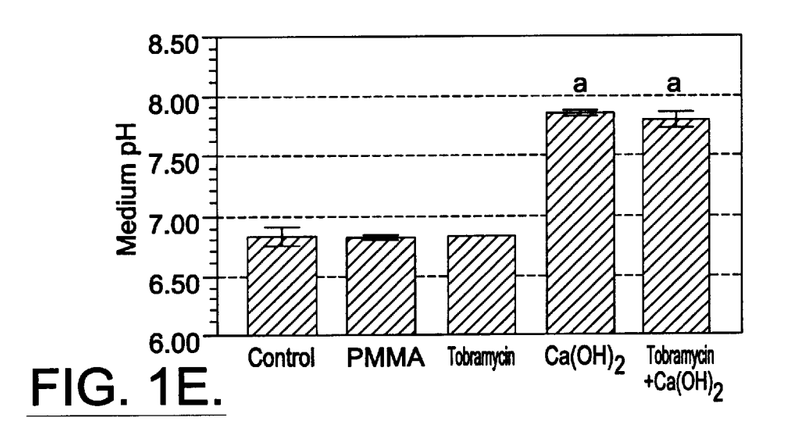
Figure 1F:
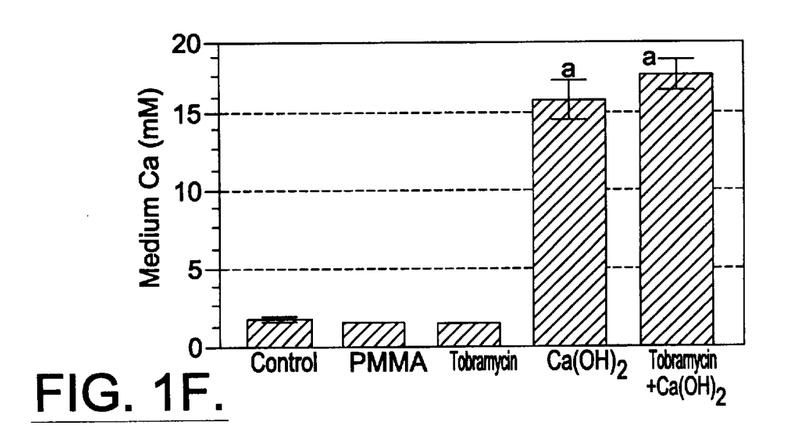

FIGS. 1D–F depict medium changes in tobramycin concentration, pH, and calcium concentration at day 3. There was a small, but significant (p<0.05), rise in tobramycin release from combination beads compared to the tobramycin beads (FIG. 1D). The elevations of pH and calcium concentration in the medium from the $Ca(OH)_2$ and $Ca(OH)_2$-tobramycin groups were significantly different compared to the control group (p<0.05). Incubating with $Ca(OH)_2$-impregnated beads in the medium for 3 days resulted in a medium pH of 7.81±0.03 (mean±95% Cl/2, FIG. 1E) in spite of the high lactic acid production by the bones in this group (FIG. 1A). Without $Ca(OH)_2$ release from beads, the pH of the medium decreased from an initial pH of 7.40 to 6.84±0.04, 6.82±0.02, and 6.84±0.01 (mean±95% Cl/2) in the control, PMMA, and tobramycin groups, respectively. Eluting Ca(OH)$_2$ from the beads for 3 days also resulted in very high calcium accumulations in the medium, i.e., 16.2±0.7 and 17.9 ±0.5 mM (mean±95% Cl/2) for Ca(OH)$_2$ beams and tobramycin plus Ca(OH)$_2$ beads, respectively, compared to 1.25 mM in the control group (FIG. 2F).

Preliminary testing has shown that using calcium hydroxide percentages less than 10% results in a release rate that is no sufficient to cause the desired stimulation of bone metabolism. The disadvantage of using a percentage more than about 20% is that maximal effects on bone are at 15% and higher percentages of calcium hydroxide will decrease the mechanical properties of PMMA and may be toxic to bone.

Figure 3:
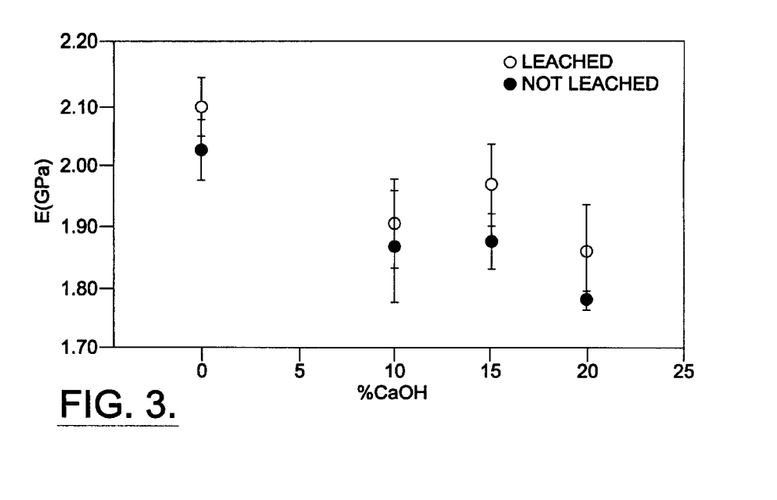
FIG. 3 illustrates the Modulus of Elasticity of a polymethylmethacrylate bone composition containing various levels of calcium hydroxide with or without leaching for twelve days.
Figure 4:
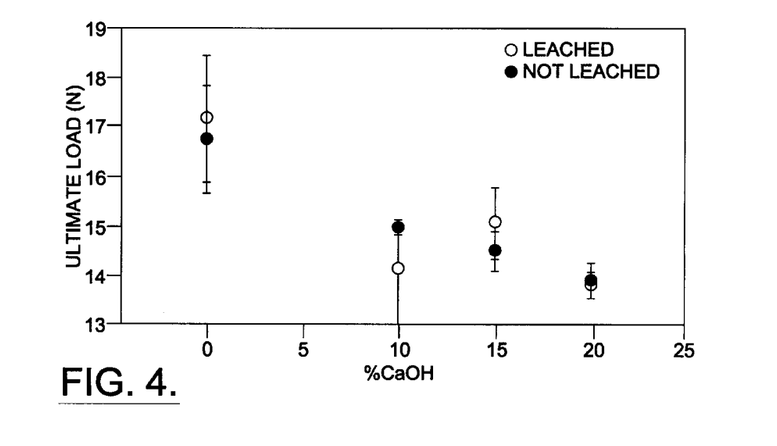
FIG. 4 illustrates the ultimate loading of in a polymethylmethacrylate bone cement composition.

Preliminary strength testing using the calcium hydroxide percentages showed ultimate strength decreases of 11–20% for leached and nonleached samples (FIG. 4) and stiffness decreases of 7–11%, as shown in FIG. 3. Leaching did not significantly affect these variables.

Preliminary strength testing using the calcium hydroxide percentages showed ultimate strength decreases of 11–20% for leached and non-leached samples and stiffness decreases of 7–11%, as shown in FIG. 3. Leaching did not affect these variables.

The advantage of adding calcium hydroxide, a stable, strong inorganic base, to bone cement is that it is released slowly at constant rate over long periods and can promote bone growth and healing in compromised areas.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A bone cement composition comprising:
   polymethylmethacrylate and an ester or amide of methacrylic acid in a combined total of from about 70% to about 90% by weight based on the total weight of the bone cement composition;
   from about 10% to about 17% by weight of calcium hydroxide; and
   a catalyst for curing the bone cement composition;
   wherein said composition when cured forms a bone cement having porous cavities encapsulating calcium hydroxide particles which are dissolvable and releasable from said porous cavities in an animal body.

2. The bone cement composition of claim 1, wherein said ester of methacrylic acid is an alkyl methacrylate.

3. The bone cement composition of claim 1, wherein said ester of methacrylic acid is methymethacrylate.

4. A bone cement composition comprising of:
   a combined total of from about 70% to about 90% by weight of polymethylmethacrylate and an ester of methacrylic acid;
   from about 10% to about 17% by weight of calcium hydroxide;
   a catalyst for curing said bone cement composition; and
   a pharmaceutically effective amount of an antibiotics.

5. The bone cement composition of claim 4, wherein said ester of methacrylic acid is an alkyl methacrylate.

6. The bone cement composition of claim 4, wherein said antibiotics is tobramycin.

7. The bone cement composition of claim 4 further comprising from about 1% to about 20% of a radiopacity additive.

8. A bone cement comprising:
   from about 70% to about 90% by weight of a polymer matrix formed from a composition consisting essentially of polymethylmethacrylate, an ester or amide of methacrylic acid, and a catalyst, said polymer matrix having porous cavities therein; and
   from about 10% to about 17% by weight of calcium hydroxide particles encapsulated within said porous cavities, said calcium hydroxide being dissolvable and releasable from said porous cavities in an animal body.

9. The bone cement according to claim 8 wherein said ester of methacrylic acid is methylmethacrylate.

10. The bone cement according to claim 8 further comprising from about 1% up to about 20% of a radiopacity additive.

11. The bone cement according to claim 8 further comprising a pharmaceutically effective amount of an antibiotic.

12. The bone cement according to claim 11, wherein said antibiotic is tobramycin.

13. A method for preparing a bone cement comprising:
    providing a mixture comprising polymethylmethacrylate, calcium hydroxide, and a polymerization catalyst;
    providing an ester or amide of methacrylic acid;
    admixing said ester of methacrylic acid and said mixture to polymerize said ester or amide of methacrylic acid and said polymethylmethacrylate,
    wherein a bone cement is formed having from about 70% to about 90% by weight of a polymer formed from said polymethylmethacrylate and said ester or amide of methacrylic acid, and from about 10% to about 17% by weight of calcium hydroxide particles, said polymer having porous cavities therein and said calcium hydroxide particles being encapsulated within said porous cavities and being dissolvable and releasable from said porous cavity in an animal body.

14. The method of claim 13, wherein said ester of methacrylic acid is an alkyl methacrylate.

15. The method of claim 13, wherein said mixture further comprises a pharmaceutically effective amount of antibiotics.

16. The method of claim 13, wherein said mixture further comprises a radiopacity additive.

17. A method for repairing a bone defect in a mammal comprising:
    providing a bone cement composition comprising of a combined total of from about 70% to about 90% by weight of polymethylmethacrylate and an ester of methacrylic acid, from about 10% to about 17% by weight of calcium hydroxide particle, and a catalyst for curing said bone cement composition;
    curing said bone cement composition; and
    implanting the cured bone cement to the area of defective bone to be repaired in said mammal.

18. The method of claim 17, wherein said ester of methacrylic acid is an alkyl methacrylate.

19. The method of claim 17, wherein said bone cement composition further comprises a pharmaceutically effective amount of an antibiotics.

20. The method of claim 19, wherein said antibiotics is tobramycin.

21. The method of claim 17, wherein said bone cement composition further comprises a radiopacity additive.

22. The method of claim 17, wherein said calcium hydroxide being dissolvable and releasable from said cured bone cement in said area of defective bone to be repaired in said mammal.

23. The bone cement composition of claim 1, further comprising from about 1% to about 20% of a radiopacity additive.

* * * * *

UNITED STATES PATENT AND TRADEMARK OFFICE
CERTIFICATE OF CORRECTION

PATENT NO. : 5,968,999
DATED : October 19, 1999
INVENTOR(S) : Ramp et al.

It is certified that error appears in the above-identified patent and that said Letters Patent is hereby corrected as shown below:

Title page, References Cited [56], U.S. PATENT DOCUMENTS, line 1, "Rees" should read --Rees et al.--; line 4, "Kato" should read --Kato et al.--; line 6, "kishida" should read --Kishida et al.--; line 8, "Kato" should read --Kato et al.--; line 10, "Sander" should read --Sander et al.--.

Title page, References Cited [56], FOREIGN PATENT DOCUMENTS, line 1, "European Pat. Off." should read --United Kingdom--.

Title page, References Cited [56], OTHER PUBLICATIONS, line 3, "Bone Miner." should read --Bone and Mineral--; line 10, "Hyudroxide" should read --Hydroxide--.

Column 5, line 58, after "comprising" cancel "of"; line 65, after "of" cancel "an".
Column 6, line 50, after "comprising" cancel "of"; line 63, after "of" cancel "an".

Signed and Sealed this

Nineteenth Day of September, 2000

*Attest:*

Q. TODD DICKINSON

*Attesting Officer*     *Director of Patents and Trademarks*